US009452085B2

(12) United States Patent
Gisquiere

(10) Patent No.: US 9,452,085 B2
(45) Date of Patent: Sep. 27, 2016

(54) DEVICE FOR SEPARATING, AND MAINTAINING A DISTANCE BETWEEN, A PERSON'S FACE AND A PROTECTIVE EYE MASK HELD IN PLACE BY AN ELASTIC STRAP

(75) Inventor: Serge Gisquiere, Pernes les Fontaines (FR)

(73) Assignee: AIRFLAPS, Paris (FR)

( * ) Notice: Subject to any disclaimer, the term of this patent is extended or adjusted under 35 U.S.C. 154(b) by 842 days.

(21) Appl. No.: 13/698,716

(22) PCT Filed: May 19, 2011

(86) PCT No.: PCT/FR2011/000303
§ 371 (c)(1),
(2), (4) Date: Nov. 21, 2012

(87) PCT Pub. No.: WO2011/144827
PCT Pub. Date: Nov. 24, 2011

(65) Prior Publication Data
US 2013/0139288 A1 Jun. 6, 2013

(30) Foreign Application Priority Data

May 21, 2010 (FR) ..................................... 10 02148

(51) Int. Cl.
*A61F 9/02* (2006.01)
*A42B 3/18* (2006.01)

(52) U.S. Cl.
CPC ............... *A61F 9/027* (2013.01); *A42B 3/185* (2013.01)

(58) Field of Classification Search
CPC ............................... A42B 3/185; A61F 9/027
See application file for complete search history.

(56) References Cited

U.S. PATENT DOCUMENTS

| 3,613,115 A | * | 10/1971 | Hill | ......................... | A61F 9/025 |
| | | | | | 2/10 |
| 4,193,133 A | * | 3/1980 | Laibach | .................. | A42B 3/185 |
| | | | | | 2/10 |
| 4,391,498 A | * | 7/1983 | Rengstorff | ............. | G02C 3/003 |
| | | | | | 351/111 |
| 4,686,712 A | * | 8/1987 | Spiva | ..................... | A42B 3/185 |
| | | | | | 2/10 |

(Continued)

FOREIGN PATENT DOCUMENTS

| DE | 102005058393 A1 | 8/2006 |
| EP | 1702596 A2 | 9/2006 |
| WO | 0189333 A1 | 11/2001 |

OTHER PUBLICATIONS

International Search Report issued Sep. 29, 2011 re: PCT/FR2011/000303; pp. 6 citing: WO 01/89333 A1, EP 1 702 596 A2, US 2008/034480 A1, U.S. Pat. No. 5,642,178 A, DE 10 2005 058393 A1 and U.S. Pat. No. 4,686,712 A.

*Primary Examiner* — Danny Worrell
(74) *Attorney, Agent, or Firm* — Cantor Colburn LLP

(57) ABSTRACT

A device for moving and maintaining apart from a face an eye protection mask with an elastic headband when the device is worn on a helmet, the device being configured to be placed between the elastic headband and the helmet, the device including two symmetrical elements each including a flap jointed on a support through an axis and provided with a lever allowing actuation of the flap, the flap being movable in rotation around the axis between a first position towards the front of the helmet with regards to the axis and a second position towards the back of the helmet with regards to the axis, where the flap is maintaining the eye protection mask apart from a face in the second position, and where the lever is in abutment against the mask in the second position.

9 Claims, 3 Drawing Sheets

(56) References Cited

U.S. PATENT DOCUMENTS

| | | | | |
|---|---|---|---|---|
| 4,796,308 A * | 1/1989 | Bourgeois | A42B 3/185 | 2/10 |
| 5,181,280 A * | 1/1993 | Zachry, Jr. | A44B 11/12 | 2/452 |
| 5,611,644 A * | 3/1997 | Lutz | A44B 11/12 | 128/207.14 |
| 5,636,388 A * | 6/1997 | Hodges | A42B 3/185 | 2/443 |
| 5,642,178 A | 6/1997 | Leonardi et al. | | |
| 5,666,663 A * | 9/1997 | Bolle | A62B 18/082 | 2/10 |
| 5,727,940 A * | 3/1998 | Wanzenbock | A61C 7/06 | 24/68 CD |
| 5,809,580 A * | 9/1998 | Arnette | A61F 9/027 | 2/426 |
| 5,937,439 A * | 8/1999 | Barthold | A42B 3/04 | 2/10 |
| 5,956,778 A * | 9/1999 | Godoy | A63B 33/002 | 2/428 |
| 6,047,410 A * | 4/2000 | Dondero | A61F 9/027 | 2/426 |
| 6,131,246 A * | 10/2000 | Paulson | A61F 9/027 | 24/265 BC |
| 6,428,167 B1 * | 8/2002 | Leonardi | A61F 9/027 | 132/273 |
| 6,490,729 B1 * | 12/2002 | Dondero | A42B 3/185 | 2/10 |
| 6,691,378 B1 * | 2/2004 | Chou | A63B 33/002 | 2/428 |
| 6,694,530 B2 * | 2/2004 | Maloney | A42B 3/185 | 2/10 |
| 6,715,157 B2 * | 4/2004 | Mage | A61F 9/029 | 2/426 |
| 6,826,785 B2 * | 12/2004 | McNeal | A44B 11/12 | 2/452 |
| 6,845,548 B1 * | 1/2005 | Lin | A42B 3/185 | 2/10 |
| 7,331,065 B1 * | 2/2008 | Chen | A61F 9/025 | 2/448 |
| 7,340,804 B2 * | 3/2008 | Saderholm | A44B 11/06 | 2/426 |
| 7,356,854 B2 * | 4/2008 | Sheldon | A61F 9/027 | 2/448 |
| 7,836,561 B2 * | 11/2010 | Vaccaro | A63B 33/002 | 2/450 |
| 9,072,331 B2 * | 7/2015 | McNeal | A42B 3/185 | |
| 2003/0041420 A1 * | 3/2003 | Kosh | A44B 11/12 | 24/193 |
| 2008/0034480 A1 | 2/2008 | Chen | | |

* cited by examiner

DEVICE FOR SEPARATING, AND MAINTAINING A DISTANCE BETWEEN, A PERSON'S FACE AND A PROTECTIVE EYE MASK HELD IN PLACE BY AN ELASTIC STRAP

TECHNICAL FIELD

The present invention relates to a device for moving apart and maintaining apart from the face an eye protection mask maintained by an elastic headband (of the ski or motocross type) when the latter is worn on a helmet.

BRIEF DISCUSSION OF RELATED ART

Two essential reasons motivated its invention:

The first is involved upon taking off its helmet. In order to optimize their efficiency, the protective masks fit at best the shape of the face by means of the elastic headband and of the seal foams. Taking off the helmet is consequently very uncomfortable—or even painful or definitely impossible—without its wearer having been rid of said mask beforehand.

The described device gives the possibility of sufficiently moving the mask apart from the face in order to take off the helmet while maintaining the protection spectacles in their normal position on the latter.

The second reason relates to the occurrence of condensation when the wearer of the mask does not perform a displacement capable of making the usual ventilation devices (orifices made in the screen or in the mounting), totally operational by means of the airflow. The present invention by moving the mask apart from the face, allows additional and sufficient airflow between the mask and the face for efficiently countering the formation of condensation on the inner face of the protective screen.

BRIEF SUMMARY

The device according to the invention gives the possibility of finding a remedy to these drawbacks. It includes, according to a first feature, two symmetrical elements placed on either side of the helmet. Each element comprises a rectangular flap, with a height slightly greater than that of the headband of the mask, pivoting around an axis. This axis secures the flap to a support, in direct contact with the helmet and not performing any movement upon actuating the flap.

For ease of understanding, we shall describe the operation of one of the two elements positioned on either side of the helmet, it being understood that the principle of the second one is exactly the same.

The element is placed between the elastic headband and the helmet, at the height of the temples, the axis being in proximity to the edge of the helmet. The axis is located perpendicularly to the elastic headband of the mask. The flap, when it is flattened against the helmet towards the rear, allows normal placement of the mask on the latter. When it is actuated from the rear to the front, the flap overcomes the elastic resistance of the headband so as to be found, after a rotation of about 180°, maintained by the headband towards the front, cantilevered with respect to the edge of the helmet. The free end of the flap then acts as a new supporting point for the mask. When each of the flaps is actuated on either side of the helmet, the mask is found maintained towards the front, at an approximate distance equal to the difference between the length of the flap on the one hand and the distance separating the axis of rotation from the edge of the helmet on the other hand.

In order to actuate each of the flaps, the latter are provided with a lever made in the extension of their length are so that it juts out from the edge of the elastic headband, either at the bottom of the latter or at the top. When the flap is positioned towards the front, said lever bears upon the mounting of the mask in order to form an abutment which interrupts the movement of the flap and ensures that the mounting is maintained stable.

In order to facilitates the movement of the flap, its free end is provided with a roller mounted on an axis allowing the headband of the mask to freely roll on the latter when it is actuated in one direction or the other.

According to particular embodiments:

The portion of each of the two side elements forming the support may be shaped in a flexible material, allowing close-fitting to the curve of the helmet.

The portion of each of the two side elements forming the support may be shaped, at its front end, so as to be attached and supported on the edge of the helmet in order to avoid any untimely movement of the support when the flap is manipulated.

The portion of each of the two side elements forming the support may be provided at its posterior end with an (adhesive or other) attachment system, not included in this patent in order to avoid any untimely movement of the support.

The supports and flaps making up each element of the device may be provided with edges for maintaining the headband of the mask, properly in place on the device, whether the flap is in the rear or front position.

The support and the flap may form a single part, an area of smaller thickness forming the joint.

The supports and flaps making up the device may be provided with a lug and a notch so that the flap remains flattened against the support in the rear position when no mask is laid on the helmet.

The portion of each of the two side elements forming the support may be a part forming an integral part of the helmet and shaped so as to directly receive the flap, which would be jointed therein.

Each of the two side elements of the device may be a part forming an integral part of the helmet and shaped so as to reproduce the operating principle of the adaptable device as described above.

BRIEF DESCRIPTION OF THE DRAWINGS

The appended drawings illustrate the invention.

DETAILED DESCRIPTION

Figure 1:
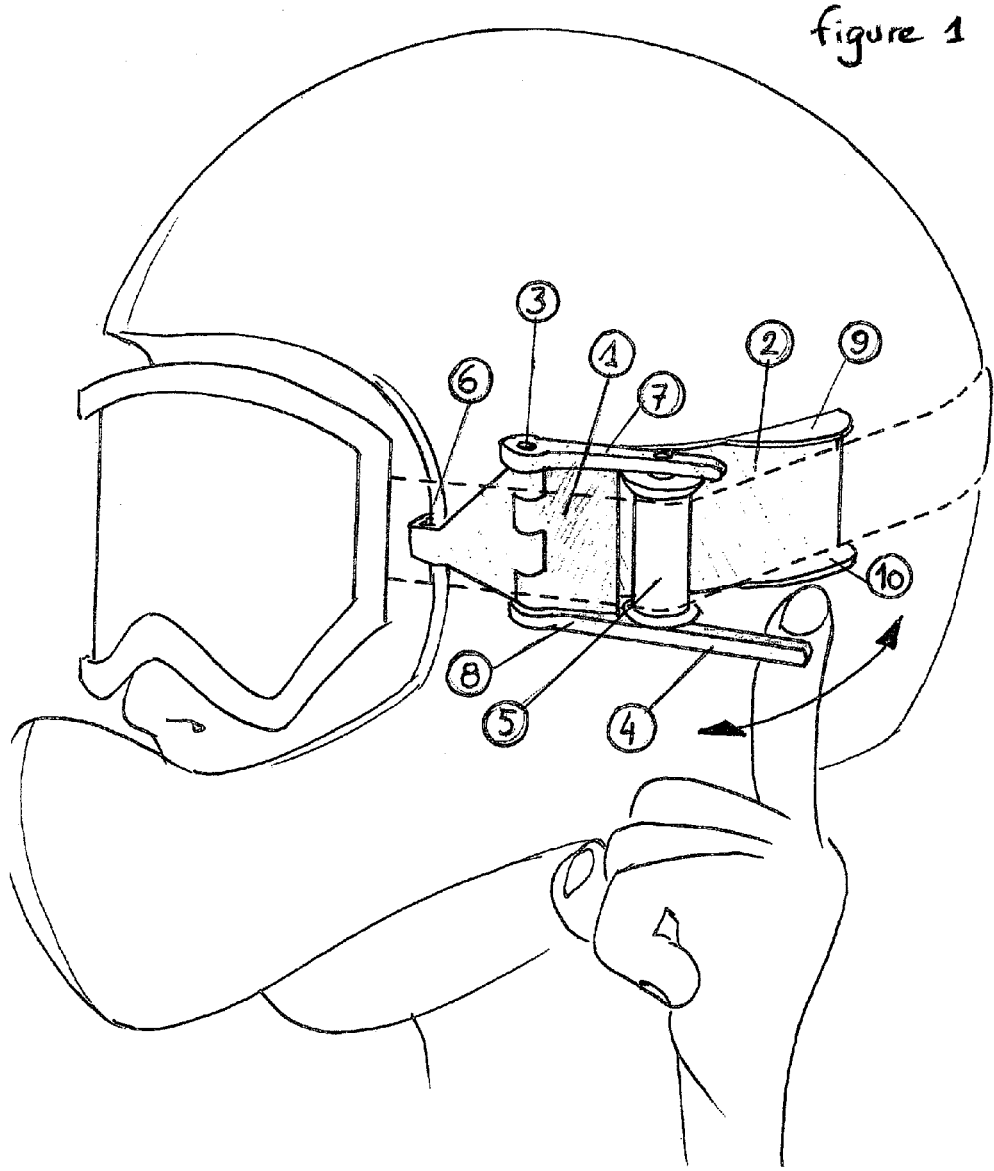
FIG. 1 illustrates the left element of the device.
Figure 2:
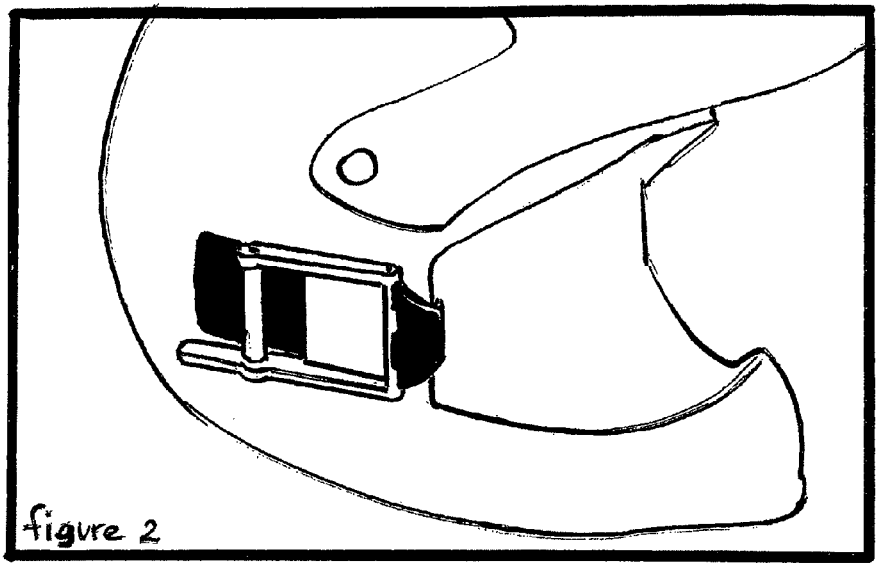
FIGS. 2 and 3 (photographs) illustrate the prototype of the right element of the device.
Figure 3:
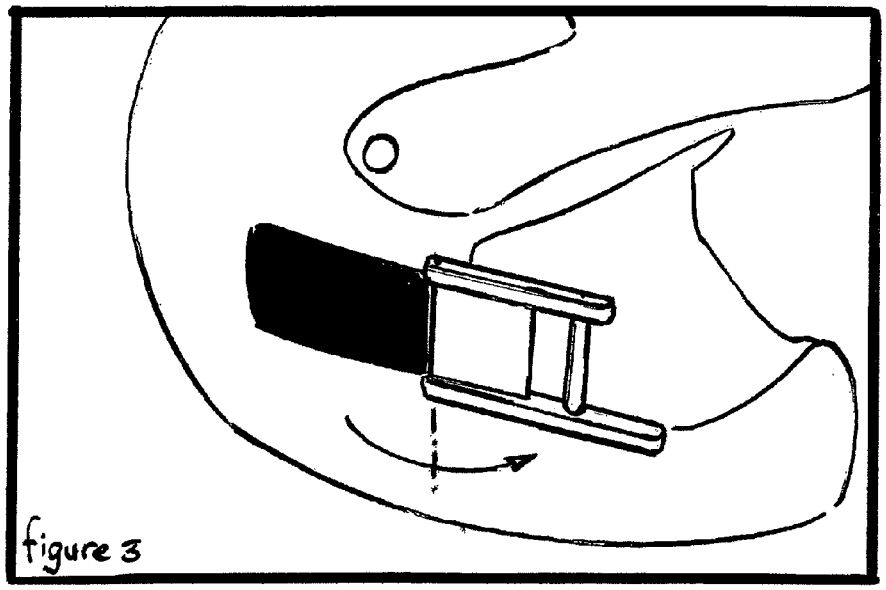
Figure 4:
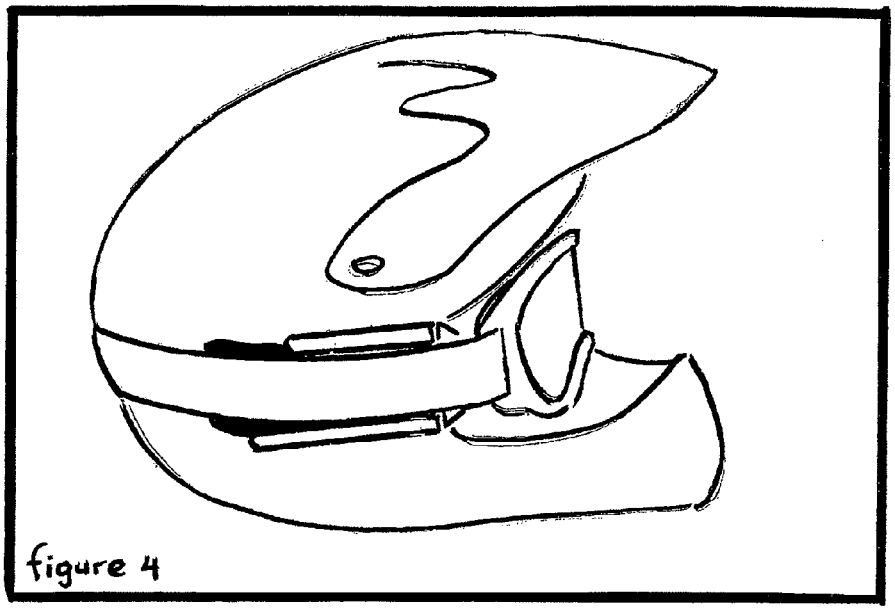
FIG. 4 (photograph) illustrates the effect of the device on a mask when the flap is in the rear position.
Figure 5:
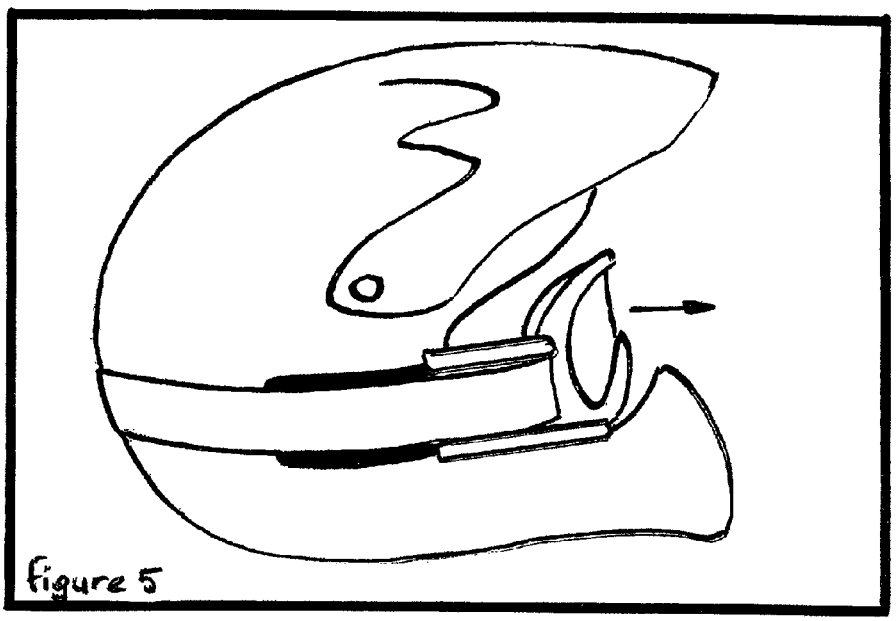
FIG. 5 (photograph) illustrates the effect of the device on a mask when the flap is in the rear position.

With reference to FIG. 1, the left element of the device has a jointed flap (1) on a support (2) through an axis (3) and provided with a lever (4) allowing the flap to be actuated and being used as an abutment on the mask when the latter is pushed back towards the front. The flap is equipped with a roller (5) mounted on an axis for facilitating the movement of the flap. The support, in its front portion, is provided with a hook (6), allowing it to be attached to the helmet and to be supported on the edge of the latter. With edges (7, 8, 9, 10), the headband of the mask may be maintained properly in place on the device whether the flap is in the rear or front position.

The invention claimed is:

1. A device for moving and maintaining apart from a face an eye protection mask with an elastic headband when said device is worn on a helmet, the device comprising
   two symmetrical elements each including a flap jointed on a support through an axis and provided with a lever allowing actuation of the flap,
   said flap being movable in rotation around said axis between a first position towards the front of the helmet with regards to the axis and a second position towards the back of the helmet with regards to the axis,
   wherein the flap is maintaining the eye protection mask apart from a face in said second position,
   wherein the lever is in abutment against the mask in said second position, and
   wherein the device being configured to be placed between said elastic headband and said helmet.

2. The device according to claim 1, wherein the flap is equipped with a roller mounted on a roller axis for facilitating movement of the flap.

3. The device according to claim 1, wherein the support, in a front portion, is provided with a hook, allowing the support to be attached to the helmet and to be supported on an edge of the latter.

4. The device according to claim 1, wherein the supports are shaped in a flexible material and have attachment devices in order to better fit a curvature of the helmet.

5. The device according to claim 1, wherein the supports and the flaps have edges with which the headband of the mask may be maintained properly in place on the device, whether the flap is in a rear or front position.

6. The device according to claim 1, wherein both flap and support form a single part, an area with smaller thickness forming the joint.

7. The device according to claim 1, wherein supports and flaps making up the device are provided with a lug and a notch so that the flap remains flattened against the support in the rear position when no mask is laid on the helmet.

8. The device according to claim 1, wherein each of two side elements of the device are a part forming an integral part of the helmet.

9. An arrangement comprising
   a device according to claim 1, and
   an eye protection mask with an elastic headband,
   said device being configured to accommodate the headband.

* * * * *